United States Patent [19]

Tsao

[11] 3,946,114

[45] Mar. 23, 1976

[54] PROCESS FOR MAKING PROTEIN FROM HYDROCARBONS

[75] Inventor: Utah Tsao, Jersey City, N.J.

[73] Assignee: The Lummus Company, Bloomfield, N.J.

[22] Filed: Nov. 5, 1973

[21] Appl. No.: 412,728

[52] U.S. Cl................. 426/60; 426/656; 195/28 R
[51] Int. Cl.²......................................... C12C 11/18
[58] Field of Search ........ 195/28 R, 37, 82, 93, 94, 195/119, 121, 74, 75, 97, 98; 426/220, 60, 204, 62, 52, 53, 54, 656, 478, 495; 260/112 R; 210/18, 42; 71/6, 25, 33

[56] References Cited
UNITED STATES PATENTS

| | | | |
|---|---|---|---|
| 2,609,328 | 9/1952 | Reed................................. | 195/74 X |
| 3,650,686 | 3/1972 | Hudson et al..................... | 210/42 X |
| 3,764,474 | 10/1973 | Watanabe et al................. | 195/28 R |

Primary Examiner—A. Louis Monacell
Assistant Examiner—R. B. Penland
Attorney, Agent, or Firm—Richard J. Holton; Alice L. Chen; Michael Klotz

[57] ABSTRACT

Yeast is produced by fermenting hydrocarbons in an aqueous nutrient medium which includes sulfate, chloride and phosphate ions. When the fermentation is completed the nutrient medium has become depleted in mineral content and a large portion of it is purged. A calcium source is added to precipitate the phosphate ion out as calcium phosphate. The precipitated calcium phosphate is added to the yeast, which in itself is an excellent source of protein. The resulting product is suitable for use as an enriched animal feed. Meanwhile the removal of the phosphate ion eliminates a pollutant from the purge stream.

4 Claims, 2 Drawing Figures

PROCESS FOR MAKING PROTEIN FROM HYDROCARBONS

BACKGROUND OF THE INVENTION

It has been known for some time that petroproteins can be produced by certain microorganisms which have the ability to attack or metabolize hydrocarbons. For example, yeasts can grow and multiply on a relatively inexpensive material and the yeast cells are a good source of protein for food supplement. The hydrocarbons can vary from simple hydrocarbons such as isopentane of n-pentane to complex hydrocarbons as crude oil, kerosene and residual oils. Microorganisms such as Monilia Murmanica, Monilia Sitophile and Saccharomyces are all suitable. A variety of nutrient media can be used depending on the type of yeast and usually contain sodium nitrate, potassium chloride, ferrous sulfate, phosphoric acid, etc. U.S. Pat. Nos. 2,697,061 and 3,474,001 disclose production of proteins from hydrocarbons using the above-mentioned microorganism including the various compositions of the nutrient media, and the conditions of the fermentation. U.S. Pat. No. 3,121,634 teaches useful compositions of animal feed containing calcium phosphate.

It is to be noted that the nutrient medium after fermentation, though depleted in minerals, still contains enough phosphate to cause a pollution problem when discharged as a waste stream into local waters.

Since phosphates have been recognized as notorious pollutants which cause algae formation, they have been in some areas banned from use as ingredients in detergents. Prohibitions exist against discharging industrial waste containing phosphates into rivers or streams. Therefore, removal of phosphates from the purge stream is a necessity.

SUMMARY OF THE INVENTION

In accordance with the invention there is provided an improved method for preparing an animal feed enriched with calcium phosphate and treating a purge stream containing phosphate. In a process of growing yeast from hydrocarbons comprising fermenting hydrocarbons with yeast in an aqueous nutrient solution containing phosphate, and separating the yeast from a partially depleted nutrient solution, the improvement comprises introducing a source of calcium into the partially depleted nutrient solution to precipitate the contained phosphate therein as calcium phosphate, and recovering the calcium phosphate, and the yeast as product.

The object of the invention is to yield an improved yeast product and at the same time to eliminate a pollutant from the purge stream.

DETAILED DESCRIPTION OF THE INVENTION

Figure 1:
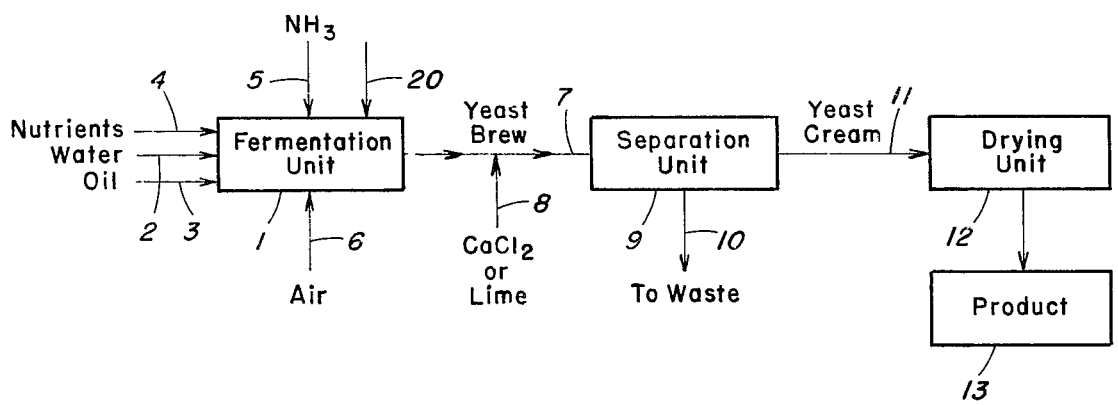
FIG. 1 is a schematic flow diagram of a batch process for the production of yeast from hydrocarbons and the recovery of phosphate as calcium phosphate.

For simplicity the description is confined to yeast, although the process is applicable to production of other proteins using nutrient media containing phosphate. Into the fermenter 1, of FIG. 1, hydrocarbon, water, nutrient medium and dried yeast are introduced through lines 3, 2, 4 and 20 respectively. For purpose of illustration, the hydrocarbon can be a n-paraffin, the nutrient medium can include potassium phosphate, phosphoric acid and potassium sulfate. Air is bubbled through line 6 into the solution for maintaining the necessary required breathing oxygen. Ammonia is added to adjust the pH to a value suitable for the innoculated yeast via line 5. The fermentation takes from a few hours to a few days during which the yeast grows. To the fermentation effluent, known as yeast brew in line 7, containing yeast and depleted nutrient, is added a required amount of calcium chloride or calcium hydroxide, or other calcium source through line 8. The resulting mixture is charged into a separating unit 9 to separate the yeast and the precipitated calcium phosphate through line 11 from the substantially phosphate-free solution, which is discharged as a waste stream through line 10. The separated enriched yeast is dried in drier 12 to form a yeast product 13 containing about 0.1 to 3.0%, preferably 1.5% by weight of calcium phosphate.

Figure 2:
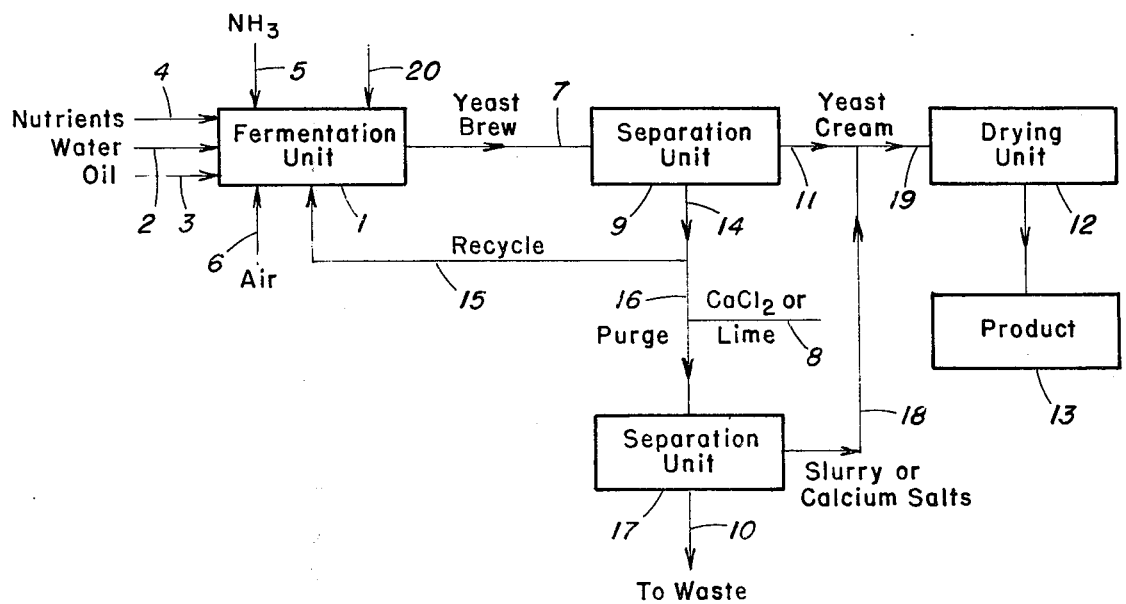
FIG. 2 is a preferred embodiment for the yeast production in a semi-continuous process.

A preferred embodiment is shown in FIG. 2 in which yeast brew from multiple fermenters 1 is collected on a staggered time basis. The yeast brew is withdrawn in rotation from each fermenter to constitute a continuous feed to the downstream yeast recovery system. This provides a semi-continuous process for use in situations involving prolonged ferementation. The same feed streams 2, 3, 4, 5, 6 and 20, as in the batch process are introduced. The yeast brew from fermenter 1 is introduced in line 7 into a separator unit 9 where yeast is centrifuged and separated from the partially depleted nutrient solution which is removed in line 14. A portion of this solution is returned to the fermenter in line 15. The remaining portion in line 16, which would otherwise have been purged as waste is now treated with a calcium source such as calcium chloride or calcium hydroxide in line 8. This precipitates the contained phosphate as calcium phosphate, which is separated by filtration or centrifugation in unit 17. The filtrate in line 10 now is substantially free of phosphate and can be discharged as a waste stream. The separated calcium phosphate is added through line 18 to the yeast in line 11 and the mixture is introduced in line 19 into a drier 12 and dried to produce a product 13 suitable for animal feed. The calcium phosphate content in this animal feed would be about 0.1 to 3.0%, preferably 1.5% by weight.

It is to be noted that in the embodiment of FIG. 2, the mineral nutrient medium in line 4 need only be make-up minerals, since the recycled nutrient in line 15 still contains a portion of the original mineral content.

It has been known that calcium phosphate can be used for animal feed in concentrations up to about 3.3% by weight phosphate. The phosphate in the enriched feed produced by the present invention is well within safe limits for animals. Of course, the content of calcium phosphate or other minerals, can easily be supplemented if desirable.

As an illustration of the present invention, the following example is included, which represents the flow rates of a process according to the embodiment shown in FIG. 2.

| Starting Materials | | |
|---|---|---|
| Hydrocarbon Oil | 11,000 lb/hr. | (line 3) |
| Net Nutrient (make-up) | 1,500 lb/hr. | (line 4) |
| Water | 110,000 lb/hr. | (line 2) |
| Calcium Chloride | 75 lb/hr. | (line 8) |
| Products | | |

-continued

| | | |
|---|---|---|
| Dried Yeast Without Calcium Salts | 10,000 lb/hr. | (line 11) |
| Dried Yeast With Calcium Phosphate Waste Stream | 10,150 lb/hr. | (line 19) |
| Purge Stream | 79,750 lb/hr. | (line 10) |

While this invention has been described with reference to certain preferred embodiments and illustrated by means of certain drawings and a specific example, it is to be understood that these are illustrative only, as many alternatives and equivalents will readily occur to those skilled in the art within the spirit and proper scope of this invention. The invention is therefore not to be construed as limited, except as set forth in the appended claims.

I claim:

1. In a process of growing yeast from hydrocarbons comprising fermenting hydrocarbons with the yeast in an aqueous nutrient solution containing phosphate, forming a yeast brew which comprises the yeast and partially depleted nutrient solution and separating the yeast from a partially depleted nutrient solution, the improvement which consists in introducing a source of calcium into the yeast brew to precipitate the contained phosphate therein as calcium phosphate, and recovering the product consisting essentially of the yeast containing calcium phosphate from the solution.

2. An improved process according to claim 1 wherein the source of calcium comprises calcium chloride.

3. An improved process according to claim 1 wherein the source of calcium comprises calcium hydroxide.

4. A process for treating a waste stream resulting from yeast fermentation in which a yeast brew comprising partially depleted nutrient solution containing phosphate and the yeast product is produced, said process consisting in introducing a source of calcium into said yeast brew to precipitate the contained phosphate therein as calcium phosphate and separating the product consisting essentially of the yeast containing calcium phosphate from the treated waste stream.

* * * * *